US012751812B2

(12) United States Patent
Cattaneo et al.

(10) Patent No.: US 12,751,812 B2
(45) Date of Patent: Oct. 6, 2026

(54) MEDICAL DEVICE FOR INTRODUCING INTO A BODILY HOLLOW VISCUS, MEDICAL SET, AND PRODUCTION METHOD

(71) Applicant: ACANDIS GMBH, Pforzheim (DE)

(72) Inventors: Giorgio Cattaneo, Karlsruhe (DE); Michael Büchert, Pforzheim (DE); Heinrich Schima, Vienna (AT); Christian Grasl, Vienna (AT)

(73) Assignee: ACANDIS GMBH, Pforzheim (DE)

( * ) Notice: Subject to any disclaimer, the term of this patent is extended or adjusted under 35 U.S.C. 154(b) by 776 days.

(21) Appl. No.: 17/299,145

(22) PCT Filed: Dec. 9, 2019

(86) PCT No.: PCT/EP2019/084196

§ 371 (c)(1),
(2) Date: Jun. 2, 2021

(87) PCT Pub. No.: WO2020/115327

PCT Pub. Date: Jun. 11, 2020

(65) Prior Publication Data

US 2022/0031444 A1 Feb. 3, 2022

(30) Foreign Application Priority Data

Dec. 7, 2018 (DE) ..................... 10 2018 131 269.5

(51) Int. Cl.

| | |
|---|---|
| ***A61F 2/07*** | (2013.01) |
| ***A61B 17/12*** | (2006.01) |
| ***A61F 2/00*** | (2006.01) |
| *A61F 2/95* | (2013.01) |
| *D01D 5/00* | (2006.01) |
| *D01D 11/06* | (2006.01) |

(52) U.S. Cl.

CPC .......... *A61F 2/07* (2013.01); *A61B 17/12118* (2013.01); *A61B 17/12168* (2013.01); *A61F 2002/0081* (2013.01); *A61F 2/95* (2013.01); *A61F 2230/0067* (2013.01); *A61F 2230/0069* (2013.01); *A61F 2240/001* (2013.01); *A61F 2250/0098* (2013.01); *D01D 5/0007* (2013.01); *D01D 11/06* (2013.01); *D10B 2331/10* (2013.01); *D10B 2509/06* (2013.01)

(58) Field of Classification Search

CPC .............. A61F 2002/077; A61F 2/0077; A61F 2002/0081; A61F 2002/0086; A61F 2/86

See application file for complete search history.

(56) References Cited

U.S. PATENT DOCUMENTS

| | | | | |
|---|---|---|---|---|
| 2002/0187288 A1* | 12/2002 | Lim | A61L 31/146 | 428/36.9 |
| 2003/0100945 A1* | 5/2003 | Yodfat | A61F 2/82 | 623/1.53 |
| 2004/0158270 A1* | 8/2004 | Wyzgala | A61B 17/320725 | 606/170 |
| 2009/0138070 A1 | 5/2009 | Holzer et al. | | |
| 2011/0262684 A1* | 10/2011 | Wintsch | A61F 2/07 | 156/93 |
| 2013/0138202 A1 | 5/2013 | Paul et al. | | |
| 2016/0206419 A1* | 7/2016 | Hebert | A61B 17/12177 | |
| 2017/0296326 A1* | 10/2017 | Chua | A61F 2/07 | |
| 2023/0107778 A1* | 4/2023 | Cox | A61F 2/915 | 623/1.13 |

FOREIGN PATENT DOCUMENTS

| | | | |
|---|---|---|---|
| EP | 2546394 | 1/2013 | |
| EP | 2678446 | 1/2014 | |
| EP | 2946750 | 11/2015 | |
| WO | WO 02/49536 | 6/2002 | |
| WO | WO 2006/116636 | 11/2006 | |
| WO | WO 2008/151204 | 12/2008 | |
| WO | WO-2008151204 A1 * | 12/2008 | A61B 17/12172 |
| WO | WO 2011/113001 | 9/2011 | |
| WO | WO 2014/134568 | 9/2014 | |
| WO | WO 2014/177634 | 11/2014 | |
| WO | WO 2016/138221 | 9/2016 | |

OTHER PUBLICATIONS

International Search Report issued in Appl. No. PCT/EP2019/084196 (2020).

EPO Communication from corresponding application No. EP 19820702.9 (Jan. 17, 2025).

* cited by examiner

*Primary Examiner* — Leslie A Lopez

(74) *Attorney, Agent, or Firm* — Barnes & Thornburg LLP

(57) ABSTRACT

A medical device for inserting into a hollow organ of the body, said medical device having a compressible and expandable lattice structure made of webs, which are integrally connected to each other by web connectors and which bound closed cells of the lattice structure, wherein the web connectors each have a connector axis extending between two cells which, in a longitudinal direction of the lattice structure, are adjacent to each other. During the transition of the lattice structure from the production state to a compressed state, the web connectors rotate in such a way that an angle between the connector axis and a longitudinal axis of the lattice structure changes, in particular increases, during the transition of the lattice structure from a completely expanded production state to a partially expanded intermediate state.

35 Claims, 7 Drawing Sheets

MEDICAL DEVICE FOR INTRODUCING INTO A BODILY HOLLOW VISCUS, MEDICAL SET, AND PRODUCTION METHOD

This application is a U.S. nationalization under 35 U.S.C. § 371 of International Application No. PCT/EP2019/084196, filed Dec. 9, 2019, which claims priority to German Patent Application No. 102018131269.5, filed Dec. 7, 2018. The disclosures set forth in the referenced applications are incorporated herein by reference in their entireties.

The invention relates to a medical device for introduction into a hollow body organ, in particular a stent, in accordance with the preamble of the present disclosure. Furthermore, the invention relates to a medical set and a production method. An example of a medical device of the aforementioned type is known from the Applicant's document WO 2014/177634 A1.

WO 2014/177634 A1 describes a highly flexible stent which has a compressible and expandable mesh structure, wherein the mesh structure is formed in one piece. The mesh structure comprises closed cells which are each delimited by four mesh elements. The mesh structure has at least one cell ring comprises between three and six cells.

Furthermore, to the Applicant's knowledge, stents with mesh structures are known which are formed from a single wire. The wire is braided with itself in order to form a tubular network. At the axial ends of the tubular network, the wire is curved round so that loops that act atraumatically are formed. The axial ends may flare outwards in a funnel shape.

The known medical device is particularly suitable for the treatment of aneurysms in small cerebral blood vessels. Blood vessels of this type have a very small cross sectional diameter and are often highly tortuous. For this reason, the known stent is highly flexible in configuration, so that on the one hand it can be compressed to a very small cross sectional diameter and on the other hand it has a high bending flexibility which enables it to be delivered to small cerebral blood vessels.

For the treatment of aneurysms in cerebral blood vessels, it is advantageous to use stents which bridge an aneurysm and screen it from the flow of blood inside the blood vessel. To enable this, providing stents with a covering is known; it closes off the cells of the stent and thus prevents the flow of blood into an aneurysm. Coverings of this type are often produced from textile materials. In combination with the stent structure, however, this results in a relatively thick-walled stent, whereupon again, the compressibility of the stent is compromised. Thus, the covering limits compression to a small cross sectional diameter, which in turn hinders delivery of the stent to small cerebral blood vessels. The Applicant's document EP 2 946 750 B1 tackles the problem of the compressibility of a stent with a textile covering by producing fibrous strands of the textile material from loosely ordered individual filaments.

The prior art discloses textile-like structures which are suitable for covering aneurysms. In particular, EP 2 546 394 A1 discloses a covering of this type, what is known as a graft, which has an electrospun structure. In order to obtain a particularly low porosity, a plurality of layers of this electrospun structure are overlaid. However, this results in thick walls which are a problem when delivering to small, highly tortuous blood vessels.

From WO 02/49536 A2, an electrospun structure is also known which has two layers of electrospun fabric, wherein the two layers have different porosities. Here again, the walls are relatively thick and hence the compressibility of the electrospun structure is limited.

EP 2 678 466 B1 concerns a stent for neurovascular applications which is covered with a nonwoven fabric. The nonwoven fabric is produced by electrospinning and comprises a plurality of layers, wherein an inner layer is impermeable to liquid and an outer layer is sponge-like in configuration. Thus, the nonwoven fabric forms a membrane of low permeability to liquid and because of the sponge-like layer, walls are thick, which compromises the compressibility of the stent.

In the light of this prior art, the objective of the invention is to provide a medical device for introduction into a hollow body organ, in particular a stent, which can be compressed down to be very small and at the same time acts to cover an aneurysm. A further objective of the invention is to provide a production method.

In accordance with the invention, this objective is achieved in respect of the exemplary medical devices, medical sets, and production methods disclosed herein.

The inventive concept therefore pertains to a medical device for introduction into a hollow body organ, in particular a stent, with a compressible and expandable mesh structure formed from mesh elements. The mesh structure has at least one closed cell ring which comprises at most 12, in particular at most 10, in particular at most 8, in particular at most 6, directly adjacent cells in a circumferential direction of the mesh structure. The cell ring may in particular comprise at least 3 cells which are directly adjacent in a circumferential direction of the mesh structure. At least a section of the mesh structure is provided with a covering formed from electrospun fabric which has irregular pores. The covering comprises at least 10 pores with a size of at least 15 $\mu m^2$ over an area of 100,000 $\mu m^2$.

Particularly preferably, the covering has at least 10 pores with a size of at least 30 $\mu m^2$ over an area of 100,000 $\mu m^2$.

In particular, the at least 10 pores may have an inscribed circle diameter of at least 4 μm, in particular at least 5 μm, in particular at least 6 μm, in particular at least 7 μm, in particular at least 8 μm, in particular at least 9 μm, in particular at least 10 μm, in particular at least 12 μm, in particular at least 15 μm, in particular at least 20 μm. The inscribed circle diameter is the diameter of the largest possible circle which can be inscribed in the pore. In other words, the inscribed circle diameter corresponds to the external diameter of a cylinder which can just be pushed through the pore.

The invention combines a highly flexible mesh structure as a support structure with a covering which has a high permeability or porosity and is particularly thin and flexible because of its production method. In this respect, the medical device is on the whole extremely compressible and can readily be introduced into very small blood vessels.

The high flexibility of the support structure or the mesh structure is in particular achieved by the fact that the mesh structure has a closed cell ring which has at most 12 directly adjacent cells in the circumferential direction of the mesh structure. The closed cell ring also means that after partial release, the mesh structure can be pulled back into a catheter since no mesh elements which could become stuck on the tip of the catheter protrude out because of the closed structure. In particular, all of the cell rings of the mesh structure have at most 12, in particular at most 10, in particular at most 8, in particular at most 6 directly adjacent cells in the circumferential direction of the mesh structure. It is possible for all of the cell rings to comprise at least 3 cells which are directly adjacent in a circumferential direction of the mesh structure.

By limiting the cells in the circumferential direction to a cell ring, the mesh elements as well as their connectors or points of intersection are also limited. Because of the limited number of mesh elements in the circumferential direction, the mesh structure can be compressed to a small cross sectional diameter in which the mesh elements preferably lie directly adjacent to each other. Moreover, by limiting the cells in the circumferential direction, a higher bending flexibility can also be obtained so that the mesh structure, in particular even in the compressed state, can be fed by means of a catheter through narrow, highly tortuous vessels.

Preferably, the mesh elements define closed cells of the mesh structure, wherein each closed cell is delimited by four respective mesh elements. High stability of the mesh structure is obtained by means of the closed cells; this is advantageous to the function of the mesh structure as a support for the covering. In particular, a high stability in the axial direction, i.e. in the direction of a longitudinal axis of the mesh structure, is obtained, which improves delivery of the medical device through a catheter. In the radial direction, because of the closed cells, the flexibility of the mesh structure may be increased, which results in an improved radial force.

In the expanded state, the medical device in accordance with the invention can cover an aneurysm properly, but at the same time allows nutrients to be supplied to the aneurysm. In addition, the supply of nutrients to branched blood vessels and adjacent vessel inner walls is obtained by means of the medical device. The covering, which is formed by an electrospun fabric, enables an aneurysm to be covered, but at the same time allows for a certain permeability. This permeability is advantageous, so that the cells of the aneurysm wall can be supplied with nutrients. In this manner, degeneration of the cells and the risk of a possible rupture of the aneurysm is avoided.

In an electrospun fabric, pores are usually irregularly shaped. The production method does not at all permit the pores to be formed in a particular pattern or shape. Furthermore, the pore sizes can only be adjusted by means of the process parameters in order to ensure that at least a portion of the pores have a certain minimum size. In accordance with the invention, over an area of 100,000 $\mu m^2$, a minimum number of pores is present which in turn have a minimum size. Specifically, over an area of 100,000 $\mu m^2$, at least 10 pores with a size of at least 15 $\mu m^2$, in particular at least 30 $\mu m^2$, are present. In practice, this combination of a specific minimum number of pores and a minimum size for these pores has proved to be particularly necessary for sufficient blood permeability for the covering simultaneously with good coverage.

During production of the covering, the minimum size of the pores can be adjusted, in particular via the duration of the electrospinning process. In addition, the covering produced from an electrospun fabric is extremely thin and flexible, which adds to the flexibility of the mesh structure. In particular, the covering barely inhibits the mesh structure from compression, which is in contrast to prior art coverings which are produced from other textile materials. Overall, then, the entire medical device in accordance with the invention can be compressed to a much smaller cross sectional diameter, and thus can be fed by means of small catheters through particularly small blood vessels.

By means of the medical device in accordance with the invention, therefore, treatments are possible in blood vessels which could not be accessed with medical devices of the prior art which have a mesh structure and a covering. Because of the high compressibility of the device in accordance with the invention, very low delivery forces arise when delivering via a catheter. The material of the covering can also contribute to reduction of the delivery forces. In particular, the delivery forces for the device with a covering may be the same or lower, compared to delivering the mesh structure alone. In any event, the delivery forces in the device with a covering compared to delivering the mesh structure alone are at most 50%, in particular at most 25%, in particular at most 10% higher.

The advantages of the present invention are even further improved when the covering, as is preferred, comprises at least 15 pores with a size of at least 30 $\mu m^2$, in particular at least 50 $\mu m^2$, in particular at least 70 $\mu m^2$, in particular at least 90 $\mu m^2$ over an area of 100,000 $\mu m^2$. It is also advantageous for the covering to have at least 15, in particular at least 20, in particular at least 25, pores with a size of at least 30 $\mu m^2$ over an area of 100,000 $\mu m^2$.

In order to ensure that the permeability of the covering is not too high, i.e. a medically acceptable shielding of the aneurysm from the blood flow in the vessel is obtained, in a preferred variation of the invention, the pore size is at most 750 $\mu m^2$, in particular at most 500 $\mu m^2$, in particular at most 300 $\mu m^2$.

The covering may be securely connected to the mesh structure, in particular cohesively connected. In particular, the covering may be applied directly to the mesh structure. As an example, the electrospinning process may be carried out directly on the mesh structure, so that when the covering is being formed, a connection with the mesh structure is simultaneously produced. The covering may be cohesively connected to the mesh structure. As an example, the covering may be connected to the mesh structure by means of an adhesive bond. The adhesive bond may be produced via a bonding agent. As an example, the bonding agent may comprise or consist of polyurethane.

The secure connection between the covering and the mesh structure prevents detachment of the covering from the mesh structure when feeding the medical device through a catheter. At the same time, positioning of the medical device under X-ray control is facilitated, because either the mesh structure or the covering may be provided with appropriate radiographic markers. Because the relative position between the covering and the mesh structure remains constant, additional radiographic markers which could identify any relative displacement between the covering and the mesh structure are not necessary. Overall, then, the number of radiographic markers, for example radiographic marker sleeves, can be reduced, which in turn has a positive effect on the compressibility of the medical device.

The mesh elements of the mesh structure may be sheathed with a bonding agent, in particular polyurethane. In particular, the bonding agent may form the cohesive connection between the covering and the mesh structure. Preferably, the bonding agent surrounds the entire mesh element and in this manner forms a sheath for the mesh element.

In a preferred embodiment of the invention, at least sections of the mesh structure form a cylindrical and/or funnel-shaped hollow body. A substantially cylindrical hollow body enables apposition of the mesh structure against the vessel walls of a blood vessel. A funnel-shaped hollow body may, for example, be used to capture thrombi inside a blood vessel or in order to treat vessels with a varying diameter. In this regard, it should be noted that the medical device may preferably be configured as a permanent implant, in particular in the form of a permanently implantable stent, or as a thrombectomy device, wherein the thrombectomy device preferably remains securely connected to the transport wire and is only temporarily deployed in a blood vessel.

In a preferred further embodiment of the mesh structure configured as a hollow body, the hollow body is entirely perfusible along the longitudinal axis. A configuration of the mesh structure of this type enables the medical device to be used as a stent or flow diverter which barely inhibits a blood flow through the blood vessel in the longitudinal direction, but prohibits the inflow of blood into a branched aneurysm because of the covering, or at least reduces the inflow.

However, in principle, the mesh structure may also be conceived with closed ends. In particular, at least one longitudinal end of the mesh structure may be closed. It is also possible for both longitudinal ends of the mesh structure to be closed.

Preferably, the closure at the longitudinal end is accomplished by means of a funnel-shaped conflation of the mesh structure. This means that the covering can additionally be provided in the funnel-shaped region of the mesh structure.

In a preferred embodiment of the invention, the covering is disposed on an outer face of the mesh structure. In this situation, the mesh structure forms a support structure which applies a sufficient radial force to fix the covering against a vessel wall. In this regard, the support structure supports the externally disposed covering. As an alternative, the covering may also be disposed on an inner face of the mesh structure.

As an alternative or in addition, the covering may be disposed on an inner face of the mesh structure. In particular, the mesh structure may be enclosed between two coverings which are each formed by an electrospun fabric. The mesh elements of the mesh structure can therefore be completely sheathed by the electrospun fabric. Specifically, the electrospun fabric of a covering on the inner face of the mesh structure extends through the cells of the mesh structure and is connected to the electrospun fabric of a covering on the outer face of the mesh structure. The mesh elements which delimit the cells are therefore sheathed on all sides by electrospun fabric.

Preferably, the covering is formed from a synthetic material, in particular a polyurethane, in particular Pellethane (trade mark for PU from Lubrizol). Materials of this type are particularly light and can readily be produced in fine filaments by an electrospinning process. The synthetic material means that on the one hand, a particularly thin and fine-pored covering can be produced. On the other hand, the synthetic material already has a high intrinsic flexibility, so that a high compressibility of the medical device is obtained.

A contribution to the flexibility of the covering is also made when, as is preferable, the covering is formed from filaments disposed in an irregular network and which have a filament thickness of between 0.1 μm and 3 μm, in particular between 0.2 μm and 2 μm, in particular between 0.5 μm and 1.5 μm, in particular between 0.8 μm and 1.2 μm.

Particularly preferably, the medical device is a stent for the treatment of aneurysms in arterial, in particular neurovascular, blood vessels. Preferably, the blood vessels may have a cross sectional diameter of between 1.5 mm and 5 mm, in particular between 2 mm and 3 mm. It is also possible to treat blood vessels with a cross sectional diameter of 4 mm to 8 mm. Carotid arteries, for example, have cross sectional diameters of this size.

In general, the medical device may be a stent for the treatment of saccular or fusiform aneurysms. Particularly in the case of fusiform aneurysms, i.e. aneurysms which extend over the entire circumference of a blood vessel, advantageously, a deliberately fine-pored structure is used for the colonization of endothelial cells. In this manner, reconstruction of the defective vessel wall can be achieved. Specifically, the structure provided with a specific: pore size which is formed by the electrospun fabric forms a scaffold for colonization by endothelial cells which can then form a new, closed vessel wall.

In contrast to conventional flow diverter structures, the electrospun structure has openings which are delimited by intersecting metal wires. These openings vary their shape and size as a function of the vessel diameter and of the manipulation of the implant, and in this manner do not offer reproducible conditions for cell proliferation.

With regard to the permeability and regularity of the covering, advantageously, at least 60%, in particular at least 70%, in particular at least 80% of the area of the covering is formed by pores with a size of at least 5 $\mu m^2$, in particular at least 10 $\mu m^2$. In particular, at least 30% of the area of the covering may be formed by pores with a size of at least 30 $\mu m^2$. It is also possible for at least 40%, in particular at least 50%, in particular at least 60%, in particular at least 70%, in particular at least 80%, of the area of the covering to be formed by pores with a size of at least 30 $\mu m^2$. The aforementioned values have been shown to be advantageous to the production of a covering which has a specific minimum permeability, in order to obtain a sufficient supply of nutrients to the cells in an aneurysm.

In order to ensure that the covering is sufficiently dense to shield the aneurysm from the flow of blood in the blood vessel in order to prevent a further extension of the aneurysm, it has been shown to be advantageous for at most 20% of the area of the covering to be formed by pores with a size of at least 500 $\mu m^2$. Alternatively or in addition, at most 50% of the area of the covering may be formed by pores with a size of at least 300 $\mu m_2$.

In general, the mesh structure may be configured as a single-pieced mesh structure. It is also possible for the mesh structure to be formed from mutually braided wires. In this regard, in preferred embodiments, the mesh elements form webs which are coupled together by means of web connectors (one-piece mesh structure). As an alternative, the mesh elements may form wires which are braided with each other (braided mesh structure). While a braided mesh structure is characterized by a particularly high flexibility, in particular bending flexibility, a one-piece mesh structure has comparatively thin walls, so that the mesh structure has a smaller influence on the blood flow inside a blood vessel.

Particularly preferably, the braided mesh structure is formed from a single wire which is curved round at the axial ends of the tubular mesh structure and forms atraumatic end loops. The wire may have a radiopaque core material and a sheath material produced from a shape memory alloy. In particular, the volume ratio between the core material, preferably platinum, and the volume of the whole of the composite wire is between 20% and 40%, in particular between 25% and 35%.

At the axial ends, the mesh structure may flare radially, in particular in the manner of a funnel. The flaring angle is preferably between 50° and 70°, in particular between 55° and 65°. The cells may be disposed in cell rings which extend in the circumferential direction of the braided mesh structure, wherein the rings have 6 to 12 cells, in particular 6 to 10 cells.

In general, the mesh structure (one-piece or braided) is preferably self-expanding.

The covering may have an elongation at break in accordance with ASTM 412 of between 300% and 550%, in particular between 350% and 500%, in particular between 375% and 450%. The elastic modulus of the covering in accordance with ASTM 412 may be:

at 50% elongation: >15-21 MPa at 100% elongation: >18<26 MPa at 300% elongation: >32<41 MPa The Shore hardness of the covering in accordance with ASTM 2240 may be between 80 A and 85 D, in particular between 90 A and 80 D, in particular between 55 D and 75 D.

In order to improve the ability to be repositioned, after compression and renewed deployment of the mesh structure, the covering may be capable of returning its original configuration, in particular its non-folded configuration.

The filaments or monofilaments of the fabric may be securely connected to each other at their points of intersection in the fabric in order to prevent them from slipping over each other. This ensures the porosity/pore size which is established by the production process. The cohesive connection is also provided after compression, delivery through the catheter and renewed deployment of the implant in the vessel and is consistent even when a side branch is perfused through the fabric.

In addition to the pores formed by electrospinning, the fabric may also be perforated by further pores which are formed in the electrospun fabric by processing the fabric, in particular by laser cutting. In this manner, a deliberate and, if desired, regional increase of the porosity or increase in pore size is achieved after the electrospinning process. As an example, laser cut, defined pores may be formed over the entire circumference or additionally over only a portion thereof.

The fabric is preferably perforated by the further pores over at least 25%, in particular at least 40%, in particular at least 50% of the circumference of the mesh structure (10). In this regard, for example, the region opposite the neck of the aneurysm can be deliberately perforated.

At least 25%, in particular least 40%, in particular at least 50% of the circumference of the mesh structure may be free from further pores. In other words, a portion of the fabric is not post-processed or subsequently perforated. In this portion of the fabric, no further pores in addition to the pores formed by electrospinning are introduced into the fabric. In this region, the fabric consists only of the pores formed by the electrospinning. The region of the fabric which is free from further pores may be disposed in the region of the neck of the aneurysm when in the implanted state. This may be desired, for example, when an unchanged porosity of the electrospun fabric is advantageous to the treatment of the aneurysm.

A combination of regions of unaltered electrospun fabric and subsequently perforated electrospun fabric is possible.

Starting from, the axial centre of the mesh structure, the further pores may be formed in both axial directions. In a further exemplary embodiment, additional pores may be disposed proximally or distally within the cover or the fabric.

The length over which the further pores may be distributed corresponds to at least 25% of the axial length of the covering or of the fabric, in particular at least 30%, in particular at least 40%, in particular at least 50% of the axial length of the covering or of the fabric.

In order to promote perfusion, the size of the further pores may be at least 50 μm, in particular at least 100 μm, in particular at least 200 μm, in particular at least 300 μm.

The separation of the further pores with respect to each other may be at least 1 multiple, in particular at least 1.5 multiples, in particular at least 2 multiples, in particular at least 2.5 multiples of the diameter of the further pores. The term "1 multiple" means the diameter of a further pore.

When, upon expansion, the mesh structure protrudes by at least 0.25 mm, in particular at least 0.5 mm, in particular at least 1 mm into the internal profile of the mesh structure, i.e. protrudes as little as possible into the lumen of the mesh structure, the formation of folds in the cover or be fabric in the vessel is limited.

This is obtained by ensuring that upon expansion of the mesh structure, the fabric protrudes into the overall lumen by at most 10% of the overall lumen, in particular by at most 5% of the overall lumen, in particular by at most 5% of the overall lumen.

In a particularly preferred embodiment, the circumferential contour of the covering is marked at least in sections, preferably around the full circumference, by a radiopaque agent. This may, for example, be obtained by means of radiopaque wires which are woven into the mesh structure along the contour of the covering. It is also possible to obtain the contour of the covering by means of an array of radiopaque sleeves, for example Pt—Ir sleeves or crimped C sleeves.

The position of the cover or the fabric is thus sufficiently visible under X-rays that the physician can precisely position the device, even in the correct rotational position.

The fabric may itself contain a radiopaque agent. As an example, the filaments of the fabric may be filled with a material which is impermeable to X-rays, in particular with at least 10% up to a maximum of 25% of material which is impermeable to X-rays, for example barium sulphate, $BaSO_4$. The basic colour of the filaments of the fabric may be transparent; adding barium sulphate, $BaSO_4$, to it can make them appear white/yellowish.

The invention also encompasses a medical set for the treatment of aneurysms, with a main catheter, a medical device in accordance with the invention for covering an aneurysm which can be moved through the main catheter to a treatment site, wherein the device is connected to or can be connected to a transport wire, wherein the mesh structure of the device comprises webs which are connected together into one piece and which define inner cells as well as edge cells, wherein the edge cells form a closed edge cell ring at a longitudinal end of the mesh structure and which is connected to inner cells on only one side, wherein at least one inner cell of the mesh structure is at least partially, preferably to a major extent, without a covering.

In a subordinate aspect, the invention concerns a method for the production of a medical device for introduction into a hollow body organ. In particular, a method for the production of a medical device with the aforementioned features as disclosed herein. In general, the method in accordance with the invention comprises the following steps:

a. providing a compressible and expandable mesh structure formed from mesh elements, which delimit closed cells of the mesh structure, wherein each closed cell is delimited by four respective mesh elements;
b. coating the mesh structure with a bonding agent, in particular produced from polyurethane; and
c. applying a covering to the mesh structure by means of an electrospinning process.

In the method in accordance with the invention, the covering is produced directly on the mesh structure. In order to obtain a secure connection between the mesh structure and the covering, a bonding agent is employed which is preferably formed from a biocompatible synthetic material. The bonding agent acts as an adhesive and connects the covering securely to the mesh structure in this manner. In this regard, particularly advantageously, polyurethane is used as the bonding agent.

Preferably, coating of the mesh structure with the bonding agent is carried out using a dip coating process. A process of this type is particularly simple and rapid to carry out and is characterized by high process reliability. To this end, the mesh structure is dipped into a vessel filled with bonding agent so that the bonding agent is applied to the mesh elements of the mesh structure. The cells of the mesh structure generally remain free from any bonding agent, and therefore are not closed by the bonding agent.

A particularly effective attachment of the covering to the mesh structure is obtained in the method in accordance with the invention in a preferred variation, wherein the bonding agent and the covering are each produced from a synthetic material. The two synthetic materials of the bonding agent and the covering bond easily with each other, so that a secure bond with the mesh structure is obtained. This is particularly effective when the synthetic material, as provided in preferred variations, is from the same group of materials. In particular, both the bonding agent and the covering may be formed from polyurethane. Specifically, the bonding agent which is preferably applied to the mesh structure by means of a dip coating process, is essentially mechanically bonded with the mesh structure. The covering then binds cohesively to the bonding agent because the synthetic material is from the same group of materials. In total, a secure connection between the mesh structure and the covering is produced in this manner.

It is also possible for application of the covering to the mesh structure by the electrospinning process to be followed by a laser cutting process. Specifically, the pores of the covering are post-processed using laser cutting. In particular, the shape of the pores and/or the size of the pores may be individually adjusted by means of a laser cutting process. The pore size of individual pores may then, for example, be deliberately increased.

Furthermore, the overall covering may be structured, in particular by means of the laser cutting process. Preferably, structuring of this type is carried out at the longitudinal end of the mesh structure. In this manner, for example, the covering could be structured such that it goes up to the longitudinal ends of the mesh structure. In the central region of the covering or the mesh structure, openings may be introduced, in particular by means of laser cutting in order, for example, to allow a flow of blood into branching blood vessels.

The invention will now be explained in more detail with the aid of exemplary embodiments and with reference to the accompanying drawings, in which.

Figure 7:
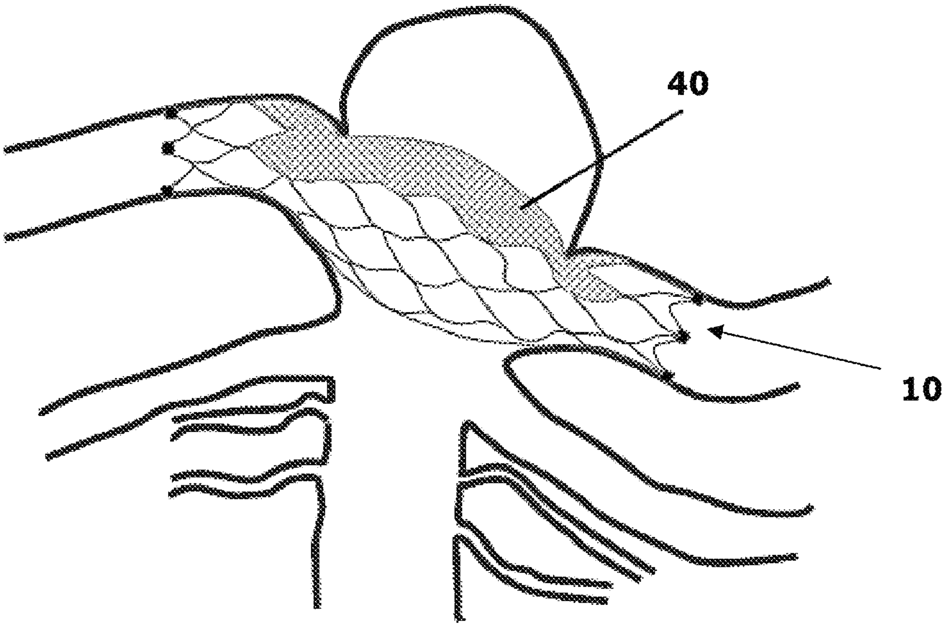
Figure 8:
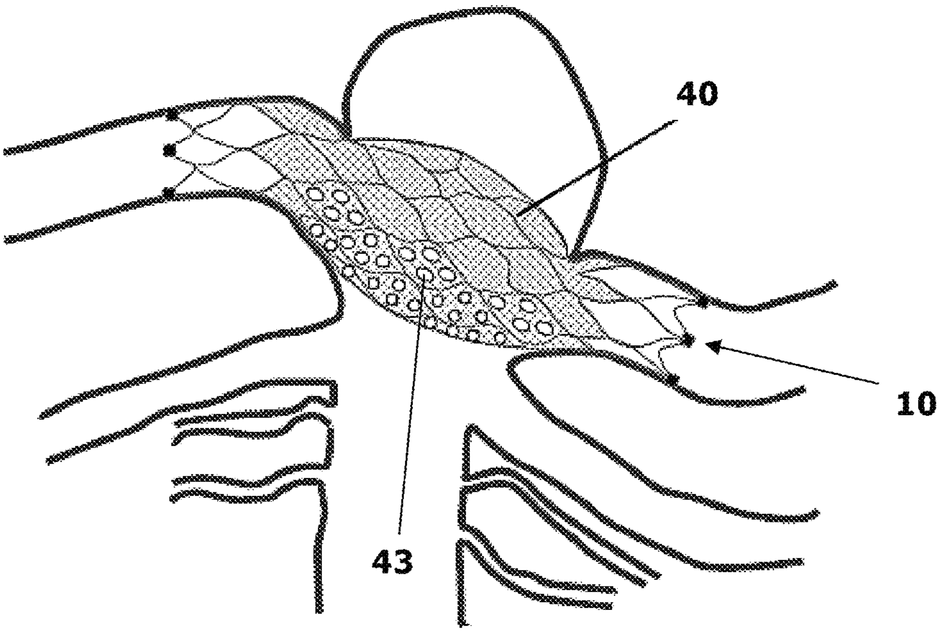

FIG. 7 shows a diagrammatic representation of a medical device in accordance with the invention according to a further preferred exemplary embodiment with a partially applied fabric in the implanted state; and FIG. 8 shows a diagrammatic representation of a medical device in accordance with the invention according to a further preferred exemplary embodiment with a partially perforated fabric, in the implanted state.

The accompanying figures show a medical device which is suitable for introduction into a hollow body organ. The medical device in this regard in particular has a mesh structure 10 which is compressible and expandable. In other words, the mesh structure 10 may take up a delivery state, in which the mesh structure 10 has a relatively small cross sectional diameter. The mesh structure 10 is preferably self-expandable, so that the mesh structure 10 can expand by itself to a maximum cross sectional diameter without the influence of external forces. The state in which the mesh structure 10 has a maximum cross sectional diameter corresponds to the expanded state. In this state, the mesh structure 10 does not exert any radial forces.

Preferably, the mesh structure 10 is one-piece in configuration. In particular, at least portions of the mesh structure 10 may be cylindrical. Preferably, the mesh structure 10 is produced from, a tubular blank by laser cutting. In this regard, individual mesh elements or webs 11, 12, 14 of the mesh structure 10 are exposed by the laser cutting process. The regions removed from the blank form, cells 30 of the mesh structure 10.

The cells 30 have a substantially diamond-shaped basic shape. In particular, the cells 30 are delimited by four respective webs 11, 12, 13, 14. The webs 11, 12, 13, 14 in the exemplary embodiment that is depicted here have an at least partially curved profile, in particular S-shaped. Other shapes for the webs are possible.

The cells 30 each have cell tips 31, 32 which form the corner points of the diamond-shaped basic shape. The cell tips 31, 32 are respectively disposed at web connectors 20 which each connect four webs 11, 12, 13, 14 together into one piece. Four respective webs 11, 12, 13, 14 extend from each web connector 20, whereupon two cells 30 are associated with each web 11, 12, 13, 14. The respective webs 12, 13, 14 delimit the cell 30.

Figure 1:
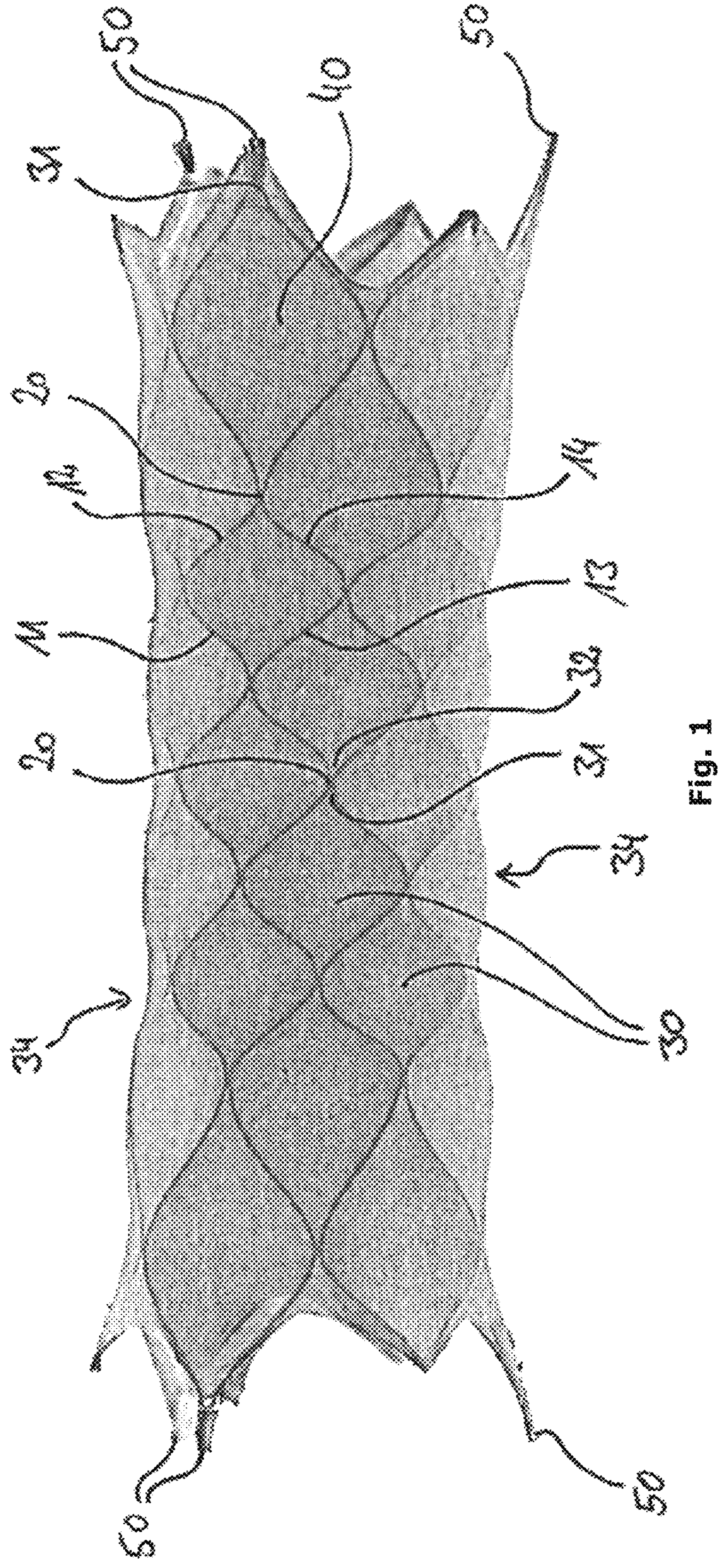
FIG. 1 shows a side view of a medical device in accordance with the invention according to a preferred exemplary embodiment.

FIG. 1 shows the mesh structure 10 in the expanded state. It can readily be seen that the web connectors 20 are substantially respectively disposed on a common circumferential line. Overall, then, a plurality of cells 30 form a cell ring 34 in the circumferential direction of the mesh structure 10. A plurality of cell rings 34 connected together in the longitudinal direction form the entire mesh structure 10. In the exemplary embodiment shown, the cell rings 34 each comprise six cells 30.

In this regard, it should be noted here that the mesh structure 10 may be formed by interconnected cell rings which have the same cross sectional diameter only in sections. Rather, it is also possible for sections of the mesh structure 10 to have a geometry which differs from that of a cylinder. As an example, the mesh structure may be funnel-shaped at least at a proximal end. A configuration of this type is advantageous in medical devices which are employed to capture thrombi or, more generally as thrombectomy devices. In these cases, the mesh structure 10 may essentially form a basket-like structure.

Mesh structures 10 which are completely cylindrical in configuration are in particular used in medical devices which form a stent. Stents can be used to support blood vessels or, more generally, hollow body organs and/or for covering aneurysms.

When the mesh structure 10 is deployed from a catheter or, more generally, a feeding system, the mesh structure 10 expands radially outwards by itself. In this regard, the mesh structure 10 passes through a plurality of levels of expansion until the mesh structure 10 reaches the implanted state. In the implanted state, the mesh structure 10 preferably exerts a radial force on the surrounding vessel walls. In the implanted state, the mesh structure 10 preferably has a cross sectional diameter which is approximately 10%-30%, in particular approximately 20% smaller than the cross sectional diameter of the mesh structure 10 in the expanded state. The implanted state is also described as the "intended use configuration".

As can readily be seen in FIG. 1, radiographic markers 50 are provided in the medical device. The radiographic markers 50 are disposed at cell tips 31, 32 on the edge cells 30 of the mesh structure 10. Specifically, the radiographic markers 50 may be formed as radiopaque sleeves, for example produced from platinum or gold, which are crimped onto the cell tips 31, 32 of the edge cells 30. In FIG. 1, it can be seen that each longitudinal end of the mesh structure 10 has three respective radiographic markers 50.

The mesh structure 10 of FIG. 1 can be divided into three sections. Two edge sections, which are each formed by two cell rings 34, are connected via a central section which comprises five cell rings 34. The cells 30 of the central section essentially have a diamond-shaped geometry, wherein all of the webs 11, 12, 13, 14 of the cells 30 of the central section have essentially the same length. The edge cell rings 34 each have cells 30 in which two of the directly adjacent webs 11, 12, 13, in the circumferential direction are each longer in configuration than the two webs 11, 12, 13, 14 of the same cell 30 which are adjacent in the axial direction. In this manner, the edge cells 30 essentially form a kite-like basic shape.

The medical device of FIG. 1 furthermore comprises a covering 40 which is disposed on an outer face of the mesh structure 10. The covering 40 bridges the entire mesh structure 10 and in particular covers the cells 30. The covering 40 is formed from an electrospun fabric and is therefore characterized by a particularly thin wall. At the same time, the covering 40 is sufficiently stable to follow an expansion of the mesh structure 10. Preferably, the covering 40 is completely and securely connected to the mesh structure 10. Specifically, the covering 40 is preferably bonded to the webs 11, 12, 13, 14, for example by means of a bonding agent which is applied to the mesh structure 10 by means of a dip coating process.

The covering 40 may extend over the entire mesh structure 10, as can be seen in FIG. 1. Alternatively, it is possible for the covering 40 to extend over only a portion of the mesh structure 10. As an example, edge cells at one axial end or at both axial ends of the mesh structure 10 may be without a covering. In this regard, the covering 40 may stop before the last or penultimate cell ring 34 of the mesh structure 10. The cell rings 34 which are without a covering allow for good coupling to a transport wire. In addition, the edge cells, which in any case barely participate in covering an aneurysm but ought to serve as anchors in a blood vessel, provide a high permeability in this manner, so that the internal walls of the vessel can be properly supplied with nutrients in this region. The region of the medical device which has the covering 40 can be highlighted by radiographic markers.

Figure 2:
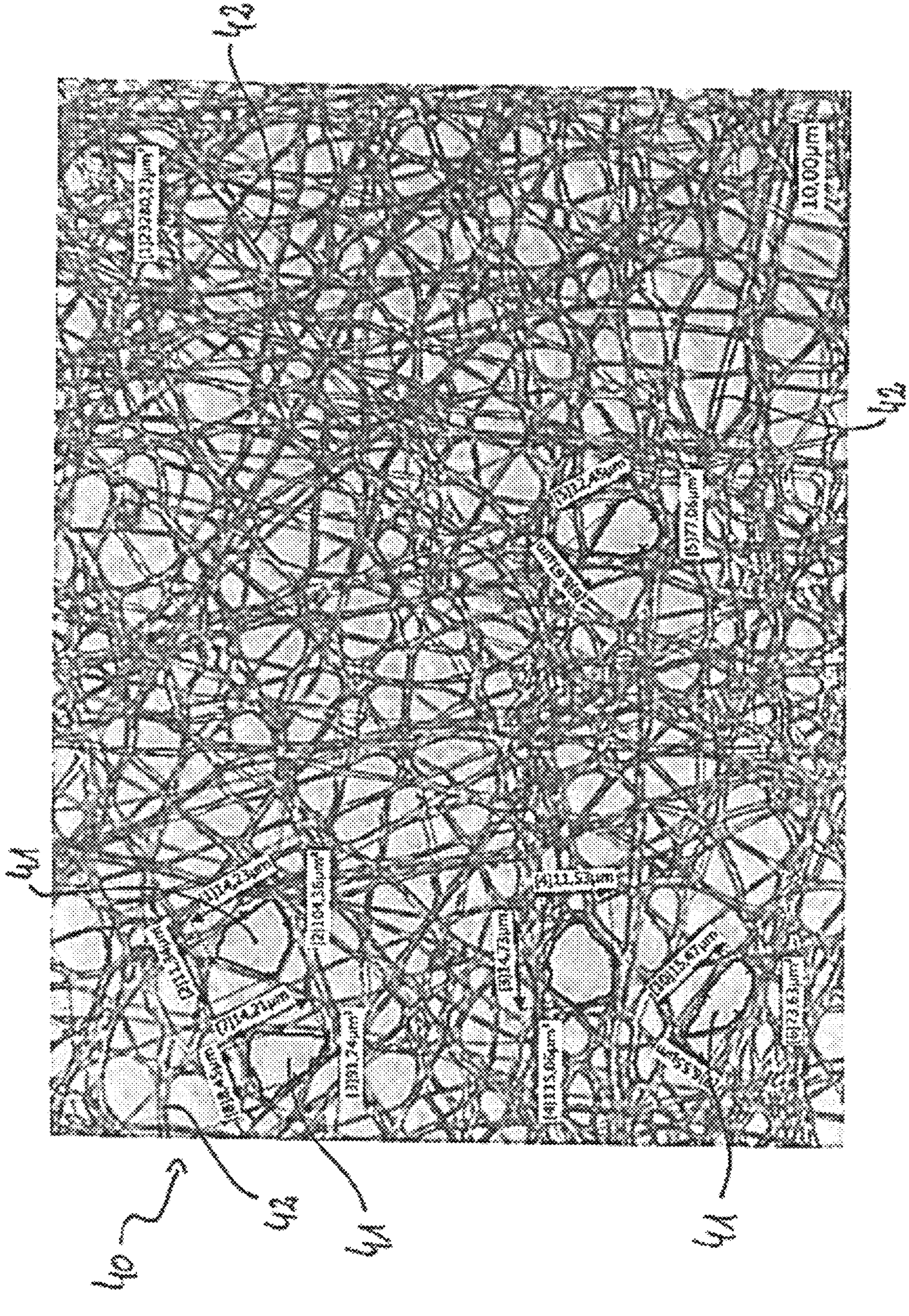
FIG. 2 shows a scanning electron microscope image of a covering of a medical device in accordance with the invention according to a preferred exemplary embodiment.
Figure 3:
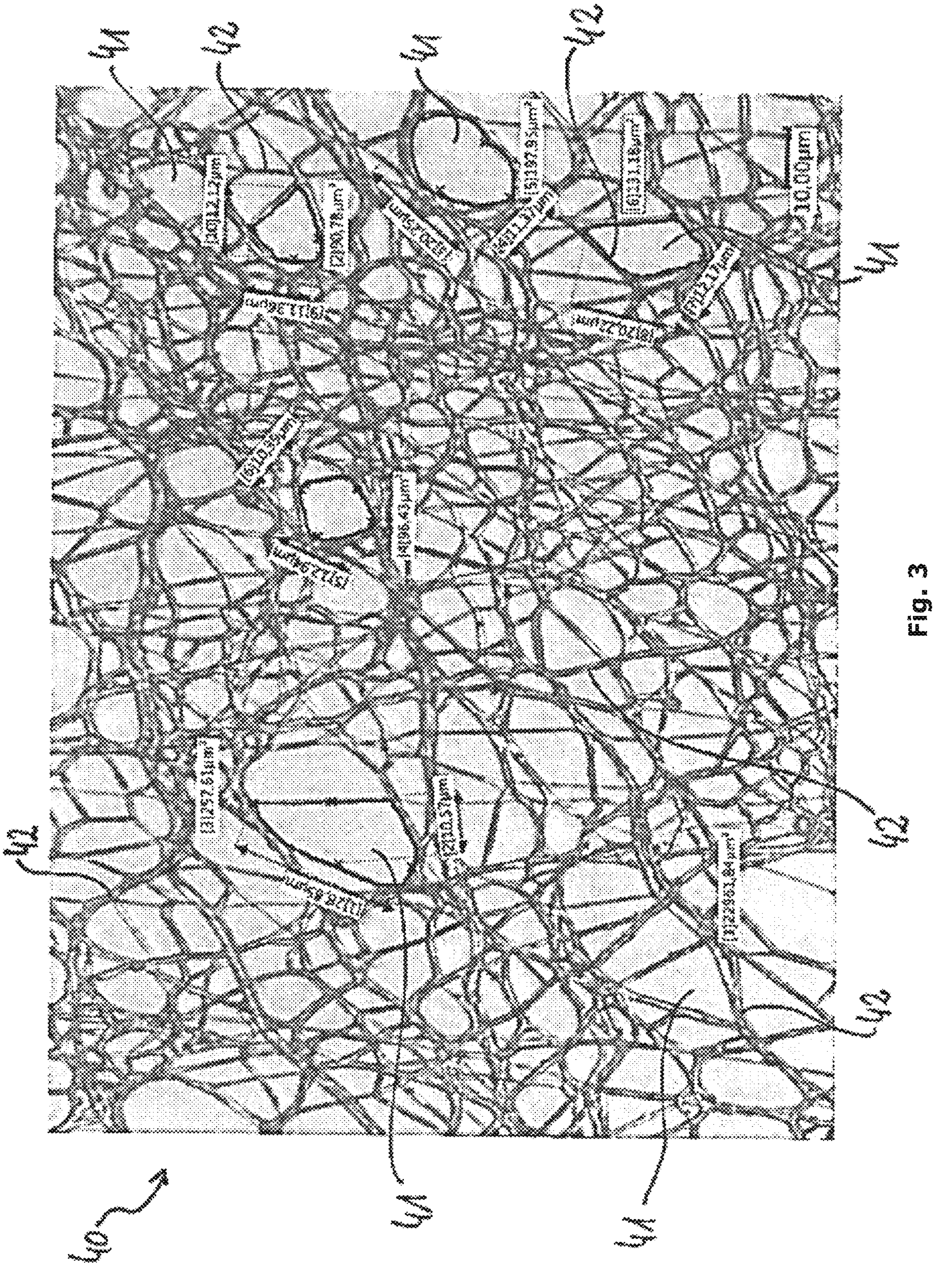
FIG. 3 shows a scanning electron microscope image of a covering of a medical device in accordance with the invention according to a further exemplary embodiment.

The configuration of the covering 40 can readily be discerned from the scanning electron microscope images of FIGS. 2 and 3. These show that the covering 40 has a plurality of irregularly sized pores 41 which are each delimited by filaments 42. By means of the electrospinning process, a plurality of filaments 42 are formed which are orientated in an irregular manner with respect to each other. This forms the pores 41. FIG. 2 also shows that the pores 41 have comparatively small pore sizes, wherein some pores 41 are sufficiently large, however, to ensure blood permeability. Specifically, in FIG. 2, four pores 41 have been graphically highlighted with a size of more than 30 $\mu m^2$. The density of the pores 41 with a size of more than 30 $\mu m^2$ indicates that the covering has at least 10 pores 41 of this type over an area of 100,000 $\mu m^2$.

FIG. 3 shows a further exemplary embodiment of a covering 40, in which a generally larger pore size has been set. It can be seen that some pores 41 have a size of more than 30 $\mu m^2$ wherein, however, a pore size of 300 $\mu m^2$ is not exceeded.

Perfusion of covered side branches (vessels) can be significantly influenced by the coating duration during production. As an example, a stent which is coated for 1 minute results in a side branch flow reduction of approximately 10-40%. As an example, a stent which is coated for 2 minutes results in a side branch flow reduction of approximately 40-70%. As an example, a stent which is coated for 4 minutes results is a side branch flow reduction of approximately 70-93%. The longer the fabric is applied to the mesh structure 10 by electrospinning using the spinning process, the denser and less porous will the fabric become. In this manner, the perfusion of side branches (vessels) can be deliberately influenced.

FIGS. 2 and 3 respectively show that the filaments 42 of the covering 40 intersect multiple times. A particular feature of the electrospinning process is, however, that in the covering 40, sites are present at which exclusively, i.e. not more than, two filaments 42 intersect. It is clear from this that the covering 40 overall has very thin walls and is therefore highly flexible.

The high flexibility of the covering 40 in combination with the high flexibility of the mesh structure 10 means that a medical device, in particular a scent, can be provided which can be introduced into a blood vessel by means of very small delivery catheters. In particular, delivery catheters can be used with a size of 6 French, in particular at most 5 French, in particular at most 4 French, in particular at most 3 French, in particular at most 2 French. Specifically, in the exemplary embodiments described herein, the medical devices can be used in catheters which have an internal diameter of at most 1.6 mm, in particular at most 1.0 mm, in particular at most 0.7 mm, in particular at most 0.4 mm.

The layer thickness of the covering 40 in particularly preferred variations is at most 10 μm, in particular at most 8 μm, in particular at most 6 μm, in particular at most 4 μm. In this, at most 4, in particular at most 3, in particular at most 2 filaments 42 intersect. In general, within the electrospun structure of the covering 40, intersecting points are present in which only 2 filaments 42 intersect. Preferably, the mesh structure 10 has a cross sectional diameter of between 2.5 mm and 8 mm, in particular between 4.5 mm and 6 mm.

Figure 4:
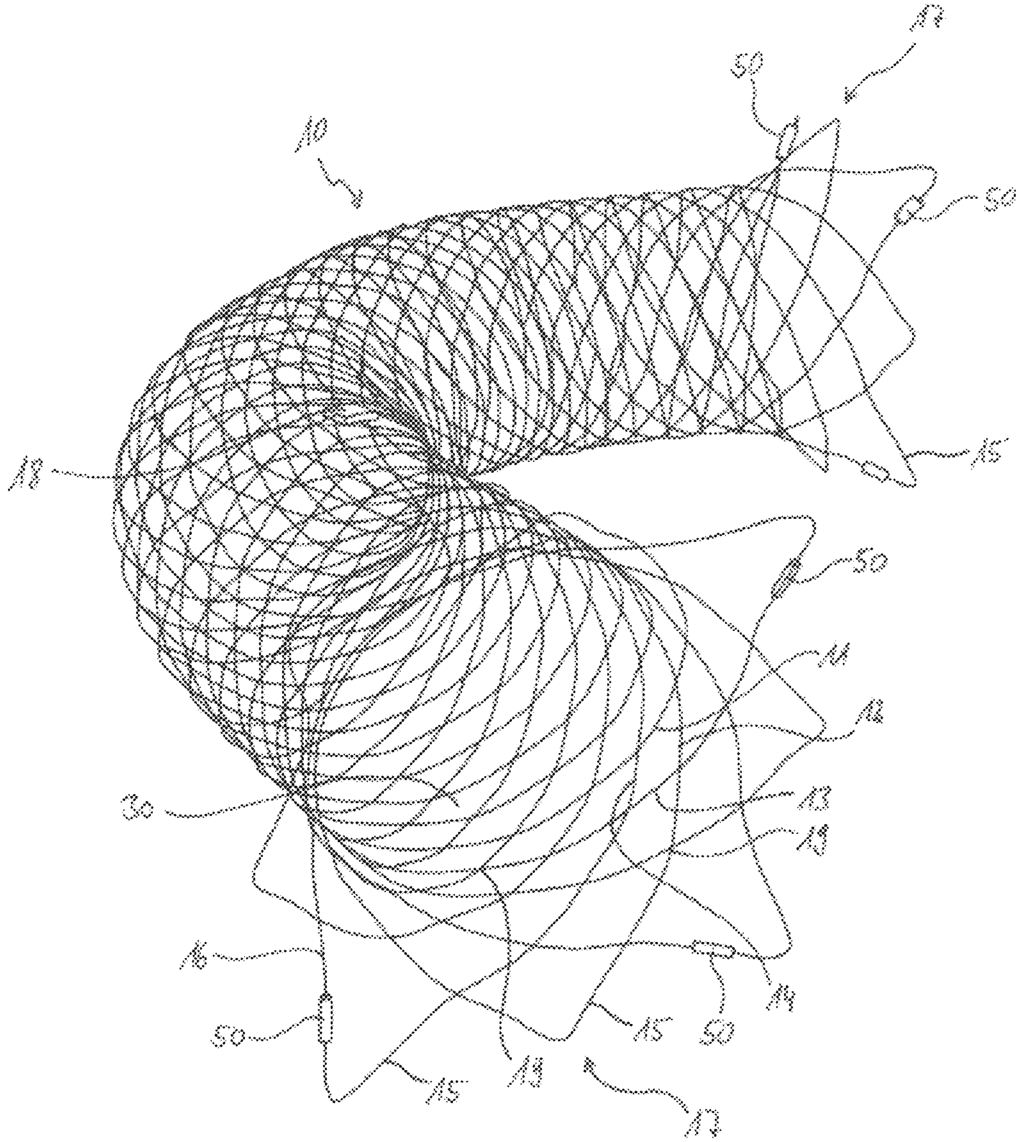
FIG. 4 shows a perspective view of a mesh structure of a medical device in accordance with the invention according to a further preferred exemplary embodiment.

FIG. 4 shows a braided mesh structure 10 which, in a preferred exemplary embodiment, can form a support for a covering 40. The braided mesh structure 10 is formed by a single wire 16 which is braided into a tube. The wire ends are connected within the mesh structure 10 with a connecting element 18.

The wire 16 has a plurality of sections which are described as the mesh elements 11, 12, 13, 14. Each section of the wire 16 which runs between two intersecting points 19 is described as an autonomous mesh element 12, 13, 14. Clearly, four respective mesh elements 11, 12, 13, 14 delimit a mesh or cell 30.

The braided mesh structure 10 has flaring axial ends which are described as flares 17. The wire 16 is turned around in each flare 17 and forms end loops 15. Overall, in the exemplary embodiment shown, six end loops 15 are provided at each flare 17. Alternate end loops 15 carry a radiographic marker 50 in the form of a crimp sleeve. Thus, three respective radiographic markers 50 are present on each axial end of the mesh structure 10.

Figure 5:
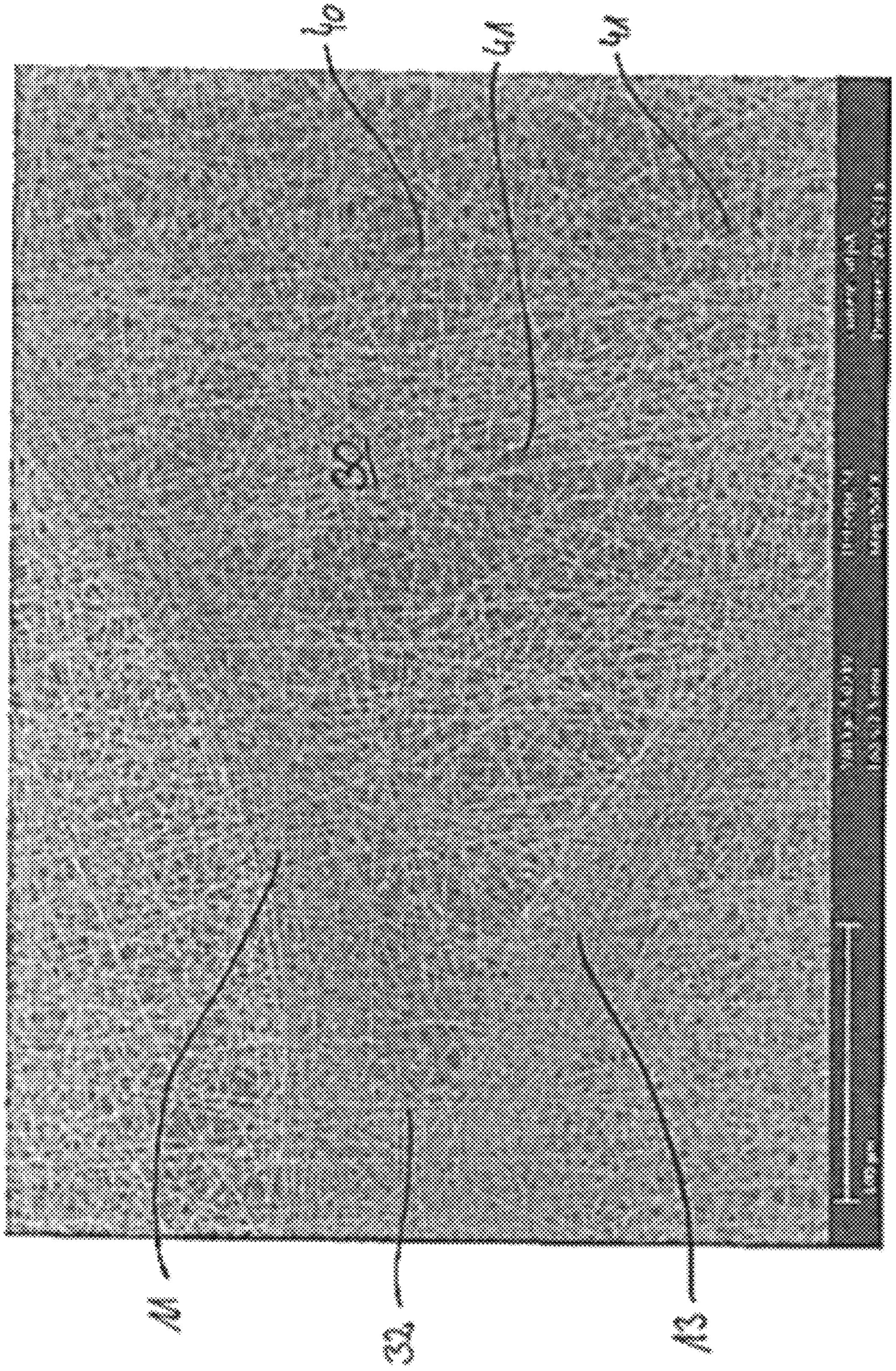
FIG. 5 shows a scanning electron microscope image of a covering of a medical device in accordance with the invention according to a further preferred exemplary embodiment, at 500× magnification.
Figure 6:
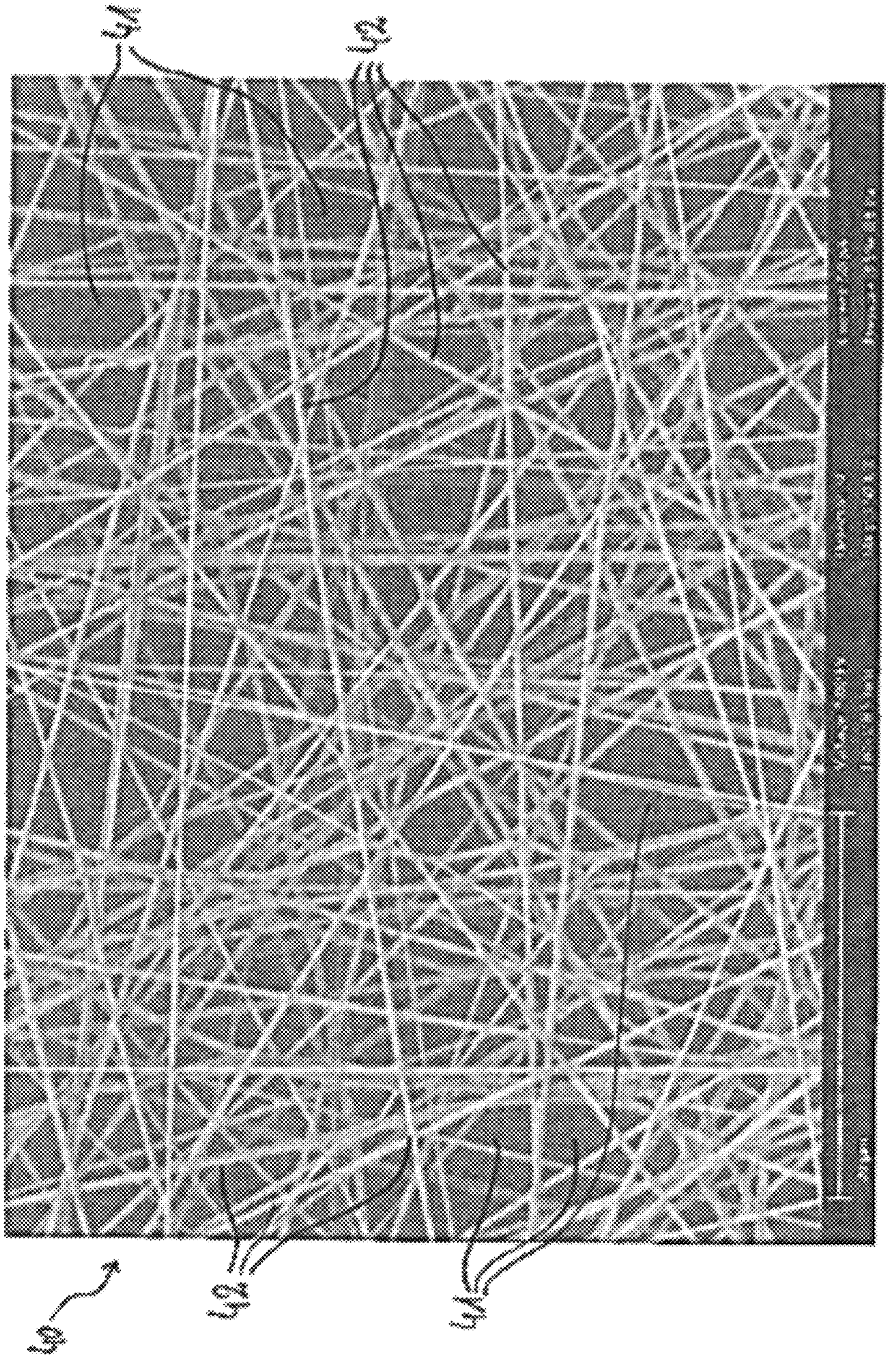
FIG. 6 shows a scanning electron microscope image of the covering of FIG. 5, under 3500× magnification.

FIGS. 5 and 6 show an exemplary embodiment of the device in accordance with the invention in different magnifications of a scanning electron microscope image. The device comprises a mesh structure 10 in accordance with FIG. 4 which is formed with a covering 40 produced from an electrospun fabric. The covering 40 is disposed on an outer face of the tubular mesh structure 10.

FIG. 5 shows a 500× magnification of a region of the device which comprises a cell tip 32 of the mesh structure 10. At the cell tip 32, two mesh elements or webs 11, 13, of a cell 30 meet. The covering 40 covers the webs 11, 12. It can be seen that the covering 40 has a plurality of pores 41, i.e. completely free through openings, of different sizes. The porosity is adjusted in this regard so that the covering 40 forms a good barrier to perfusion, but at the same time allows the passage of nutrients.

The 3500× magnification of FIG. 6 shows a section of the covering 40 of FIG. 5 in detail. The profile of the individual filaments 42 of the electrospun fabric can clearly be seen. The filaments 42 delimit pores 41, wherein the pores 41 are irregular in configuration. In each case it can be seen that some pores 41 have a larger through area than other pores 41. The larger pores 41 allow the passage of nutrients through the covering 40.

FIG. 7 shows the mesh structure 10 of an exemplary embodiment (stent) in accordance with the invention in the implanted state, wherein the covering 40 is disposed on the mesh structure 10 in the region of the aneurysm neck and bridges it. The covering 40 is disposed on a part circumference or on an angled segment of the mesh structure 10. In the example, the fabric or the covering covers approximately half the circumference of the mesh structure 10 or the stent. Another level of coverage, i.e. more or less than half the circumference of the mesh structure 10, is possible. As can be seen in FIG. 7—in contrast to FIG. 8—there are no other pores provided in the fabric apart from the pores formed by electrospinning. The properties of the fabric are therefore determined only by the pores formed during the electrospinning production process.

FIG. 8 shows a further exemplary embodiment of the invention in which, as in FIG. 7, the mesh structure 10 is implanted for the treatment of an aneurysm. In contrast to FIG. 7, the covering 40, in particular the fabric, is applied entirely around the circumference of the mesh structure 10 and in fact by electrospinning. A portion of the covering 40, specifically the portion of the covering 40 which is opposite the aneurysm neck, is perforated in addition to the pores formed by electrospinning. This is achieved by a secondary treatment of the fabric, for example by laser cutting. The further pores 43 which are formed in the fabric in this manner are larger than the pores formed by electrospinning, as can be seen in FIG. 8. In the example of FIG. 8, four further pores 43 are formed per cell. The number of further pores 43 can vary. In contrast to the pores formed by electrospinning, the further pores 43 are geometrically defined, and are circular, for example. This is made possible because of the laser cutting.

The additional perforation of the fabric enables the perfusibility of the fabric to be specifically influenced, for example in order to improve the blood supply to the side branches, without in any way compromising the treatment of the aneurysm.

REFERENCE LIST

10 mesh structure
11, 12, 13, 14 web or mesh element
15 end loop
16 wire
17 flare
18 connecting element
19 intersecting point
20 web connector
30 cell
31, 32 cell tip
34 cell ring
40 covering
41 pore
42 filament
43 further pores
50 radiographic marker

The invention claimed is:

1. A medical device for introduction into a hollow body organ with a compressible and expandable mesh structure formed from mesh elements and which has at least one closed cell ring which comprises at most 12 directly adjacent cells in a circumferential direction of the mesh structure, wherein the mesh structure is provided, at least in sections, with a covering formed from an electrospun fabric having filaments disposed in an irregular network to define irregular pores, wherein the filaments of the fabric are cohesively connected to each other at their points of intersection in the fabric, wherein at most four filaments of the filaments intersect at any respective point of intersection, wherein the covering comprises at least 10 pores of the irregular pores with a size of at least 15 $\mu m^2$ over an area of the covering extending 100,000 $\mu m^2$, wherein at least 60% of the area of the covering is formed by pores of the irregular pores with a size of at least 10 $\mu m^2$, wherein the mesh elements delimit closed cells of the mesh structure, and wherein each closed cell is delimited by four respective mesh elements of the mesh elements.

2. The medical device as claimed in claim 1, wherein the covering further comprises at least 10 pores of the irregular pores with a size of at least 30 $\mu m^2$ over the area of the covering.

3. The medical device as claimed in claim 1, wherein the at least 10 pores have an inscribed circle diameter of at least 4 μm.

4. The medical device as claimed in claim 1, wherein the covering further comprises at least 15 pores of the irregular pores with a size of at least 30 $\mu m^2$ over the area of the covering.

5. The medical device as claimed in claim 1, wherein the irregular pores of the covering each have a size that is at most 750 $\mu m^2$.

6. The medical device as claimed in claim 1, wherein the covering is securely connected to the mesh structure.

7. The medical device as claimed in claim 6, wherein the mesh elements are sheathed by a bonding agent, wherein the bonding agent forms a cohesive connection of the covering with the mesh structure.

8. The medical device as claimed in claim 1, wherein at least portions of the mesh structure form a cylindrical and/or funnel-shaped hollow body.

9. The medical device as claimed in claim 8, wherein the hollow body is entirely perfusible along a longitudinal axis.

10. The medical device as claimed in claim 8, wherein the covering is disposed on an outer face of the mesh structure.

11. The medical device as claimed in claim 1, wherein the covering is formed from a synthetic material.

12. The medical device as claimed in claim 1, wherein the filaments of the covering each have a filament thickness of between 0.1 μm and 3 μm.

13. The medical device as claimed in claim 1, wherein the medical device is a stent for treatment of aneurysms in arterial blood vessels.

14. The medical device as claimed in claim 1, wherein at least 30% of the area of the covering is formed by pores of the irregular pores with a size of at least 30 $\mu m^2$.

15. The medical device as claimed in claim 1, wherein at most 20% of the area of the covering is formed by pores of the irregular pores with a size of at least 500 $\mu m^2$.

16. The medical device as claimed in claim 1, wherein at most 50% of the area of the covering is formed by pores of the irregular pores with a size of at least 300 $\mu m^2$.

17. The medical device as claimed in claim 1, wherein the mesh elements form webs which are coupled together into one piece by means of web connectors, or form wires which are braided together.

18. The medical device as claimed in claim 1, wherein the covering has an elongation at break in accordance with ASTM 412 of between 300% and 550%.

19. The medical device as claimed in claim 1, wherein the covering has an elastic modulus in accordance with ASTM 412 as follows:

at 50% elongation: >15-21 MPa at 100% elongation: >18<26 MPa at 300% elongation: >32<41 MPa.

20. The medical device as claimed in claim 1, wherein the covering has a Shore hardness in accordance with ASTM D 2240 of between 80 A and 85 D.

21. The medical device as claimed in claim 1, wherein after compression and renewed deployment of the mesh structure, the covering is capable of returning its original configuration.

22. The medical device as claimed in claim 1, wherein in addition to the irregular pores formed by electrospinning, the fabric is also perforated by further pores which are formed in the electrospun fabric by processing the fabric.

23. The medical device as claimed in claim 22, wherein the fabric is perforated by the further pores over at least 25% of a circumference of the mesh structure.

24. The medical device as claimed in claim 22, wherein at least 25% of a circumference of the mesh structure is free from the further pores.

25. The medical device as claimed in claim 22, wherein starting from an axial centre of the mesh structure, the further pores are formed in both axial directions.

26. The medical device as claimed in claim 22, wherein the further pores each have a size that is at least 50 μm.

27. The medical device as claimed in claim 22, wherein the further pores are each separated with respect to each other by at least 1 multiple of a diameter of the further pores.

28. The medical device as claimed in claim 1, wherein on expansion of the mesh structure, the fabric remains at least 0.25 mm within an internal profile of the mesh structure.

29. The medical device as claimed in claim 1, wherein on expansion of the mesh structure, the fabric protrudes into an overall lumen of the mesh structure by at most 10% of the overall lumen.

30. The medical device as claimed in claim 1, wherein a circumferential contour of the covering is marked at least in sections by a radiopaque agent.

31. The medical device as claimed in claim 1, wherein the fabric itself contains a radiopaque agent.

32. A medical set for treatment of aneurysms, with a main catheter, a medical device as claimed in claim 1 for covering an aneurysm which can be moved through the main catheter to a treatment site, wherein the device is connected to or can be connected to a transport wire, wherein the mesh structure of the device comprises webs which are connected together into one piece and which define inner cells as well as edge cells, wherein the edge cells form a closed edge cell ring at a longitudinal end of the mesh structure and which is connected to inner cells on only one side, wherein at least one inner cell of the mesh structure is at least partially without a covering.

33. A method for the production of a medical device for introduction into a hollow body organ as claimed in claim 1, wherein the method comprises the following steps:

a. providing the compressible and expandable mesh structure;

b. coating the mesh structure with a bonding agent; and c. applying the covering to the mesh structure by means of an electrospinning process.

34. The method as claimed in claim 33, wherein coating of the mesh structure is carried out with the bonding agent by means of a dip coating process.

35. The method as claimed in claim 33, wherein the bonding agent and the covering respectively comprise a synthetic material.

* * * * *